United States Patent
Meudt et al.

(10) Patent No.: US 7,405,318 B2
(45) Date of Patent: Jul. 29, 2008

(54) METHOD FOR PRODUCING NITRILES BY ELIMINATION OF WATER FROM ALDEHYDE OXIMES WITH ALKYLPHOSPHONIC ANHYDRIDES

(75) Inventors: Andreas Meudt, Hofheim (DE); Stefan Scherer, Griesheim (DE); Claudius Boehm, Frankfurt (DE)

(73) Assignee: Archimica GmbH, Frankfurt am Main (DE)

( * ) Notice: Subject to any disclaimer, the term of this patent is extended or adjusted under 35 U.S.C. 154(b) by 132 days.

(21) Appl. No.: 11/579,938

(22) PCT Filed: Jun. 4, 2005

(86) PCT No.: PCT/EP2005/006015

§ 371 (c)(1),
(2), (4) Date: Nov. 8, 2006

(87) PCT Pub. No.: WO2005/123661

PCT Pub. Date: Dec. 29, 2005

(65) Prior Publication Data

US 2008/0033186 A1     Feb. 7, 2008

(30) Foreign Application Priority Data

Jun. 19, 2004   (DE) .................... 10 2004 029 812

(51) Int. Cl.
*C07C 255/00* (2006.01)
*C07C 253/00* (2006.01)

(52) U.S. Cl. ...................................... 558/467; 558/411

(58) Field of Classification Search ................ 558/467, 558/411
See application file for complete search history.

(56) References Cited

FOREIGN PATENT DOCUMENTS

| EP | 0 370 399 A2 | 5/1990 |
|---|---|---|
| EP | 0 550 762 A1 | 7/1993 |
| WO | WO 86/04577 A1 | 8/1986 |
| WO | WO 98/05630 A1 | 2/1998 |

*Primary Examiner*—Sikarl A Witherspoon
(74) *Attorney, Agent, or Firm*—ProPat, L.L.C.

(57) ABSTRACT

The invention relates to a method for producing the nitrites of formula: $R^1$—CN by reacting aldehyde oximes ($R^1CN$=N—OH) with cyclic alkylphosphonic anhydrides at a temperature ranging from –100 to +120° C., wherein $R^1$ represents H, a linear or branched $C_1$-$C_{12}$ alkyl group, a $C_3$-$C_{10}$ cycloalkyl, alkenyl or an aryl or heteroaryl group. The cyclic phosphonic anhydride preferably used is a 2,4,6-substituted 1,3,5,2,4,6-trioxatriphosphinane-2,4,6-trioxide of formula (I), wherein R' independently represents allyl, aryl or open-chain or branched $C_1$ to $C_{12}$ alkyl groups. Optionally, the reaction can be carried out in the presence of a tertiary amine base $NR^2_3$

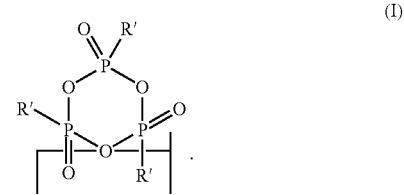

(I)

9 Claims, No Drawings

METHOD FOR PRODUCING NITRILES BY ELIMINATION OF WATER FROM ALDEHYDE OXIMES WITH ALKYLPHOSPHONIC ANHYDRIDES

CROSS-REFERENCE TO RELATED APPLICATIONS

This application is being filed under Rule 1.371 as a National Stage Application of pending International Application No. PCT/EP2005/006015 filed Jun. 4, 2005, which claims priority to the following parent application: German Patent Application No. 10 2004 029 812.2, filed Jun. 19, 2004. Both International Application No. PCT/EP2005/006015 and German Patent Application No. 10 2004 029 812.2 are hereby incorporated by reference herein in their entirety.

FIELD OF THE INVENTION

This invention relates to a method of producing nitriles. This invention more particularly relates to a method for producing nitriles by reacting aldehyde oximes with cyclic alkylphosphonic anhydrides.

BACKGROUND OF THE INVENTION

Nitriles are important and extremely versatile intermediates in organic synthesis. This compound class exhibits a high reactivity of the C,N triple bond, which enables numerous addition reactions. The significance in modern organic synthesis is restricted only by limitations of the availability of these compound classes.

Standard processes for preparing nitrites are eliminations of correspondingly functionalized aldoximes. Numerous methods, including those using acetic anhydride, acetyl chloride, thionyl chloride or lead oxide, are used. Other water-eliminating agents used have been phosphorus pentoxide, benzenesulfonyl chloride, ethyl chloroformate or aqueous alkalis. Thermal elimination at 340-360° C. over a metal oxide catalyst is likewise possible. One-pot processes starting from aldehydes also find use. However, it is always necessary to work at 70-140° C. The conversion of aldehydes using hydroxylamine hydrochloride and trifluoroacetic anhydride takes place at 20° C. Another variant is the reaction of aldehydes with hydroxylamine hydrochloride in pyridine/water in the presence of dicyclohexylcarbodiimide, Cu(II) salt and triethyl-amine. In addition to heavy metal salts, dicyclohexyl-urea which is removable only with extreme difficulty is also obtained.

In modern organic synthesis, the significance of chemo-, regio- and stereoselective reagents is increasing explosively. When, for example, the intention is to convert an oxime to a nitrile in a complex molecule with numerous functional groups, numerous methods of those mentioned are ruled out for selectivity reasons. The use of thermal dehydration is also restricted, since very high temperatures of up to 450° C. are required.

A selective and preferred method for eliminating oximes to nitrites is the reaction with a multitude of dehydrating agents.

There has to date been a lack of a highly selective solution to the problem of the transformations mentioned. Although the known reagents can accomplish the desired transformations, other moieties are often likewise influenced. In many cases, the drastic conditions required epimerize even far-removed stereocenters. In addition, the transformation should therefore be usable under very mild conditions, and particularly the removal of the conversion products of the reagent used should be very simple.

It is therefore an object of the invention to provide an economically viable process which allows the conversion of oximes to the corresponding nitrites by elimination of water, but at the same time permits the use of very mild reaction conditions and has a simplified workup.

The processes for preparing nitrites known in the prior art all have serious disadvantages:

For instance, when thionyl chloride is used, the reaction has to be performed at elevated temperature. This is disadvantageous in the case of sensitive compounds in particular. When lead oxide is used, the heavy metal is obtained in the waste stream.

Although the Voswinkel process has been found to be useful in the one-stage preparation of nitrites starting from aldehydes, the use of dicyclohexylcarbo-diimide harbors disadvantages since it is sensitizing, and it is often not possible to completely remove the reaction by-products.

SUMMARY OF ADVANTAGEOUS EMBODIMENTS OF THE INVENTION

It has been found that, surprisingly, the use of cyclic 2,4,6-substituted 1,3,5,2,4,6-trioxatriphosphinane 2,4,6-trioxides solves all of these problems. This elimination method enables the highly selective conversion of oximes to the corresponding nitrites, with simultaneous observation of the desired freedom from epimerization and maximum regio- and stereo-selectivity with simultaneously virtually quantitative yields.

DETAILED DESCRIPTION OF ADVANTAGEOUS EMBODIMENTS OF THE INVENTION

The present invention thus relates to a highly selective process for preparing nitrites of the formula (II)

$$R^1\text{—CN} \qquad (II)$$

by reacting aldehyde oximes ($R^1CH=N-OH$)

with cyclic alkylphosphonic anhydrides and optionally an amine base $NR_3^2$ at a temperature in the range from $-100$ to $+120°$ C., where $R^1$ is H, a linear or branched, substituted or unsubstituted $C_1$-$C_{12}$-alkyl radical, a $C_3$-$C_{10}$-cycloalkyl radical, alkenyl radical or an aryl or heteroaryl radical.

In a preferred inventive embodiment, the cyclic alkylphosphonic anhydride is a 2,4,6-substituted 1,3,5,2,4,6-trioxatriphosphinane 2,4,6-trioxide of the formula (I)

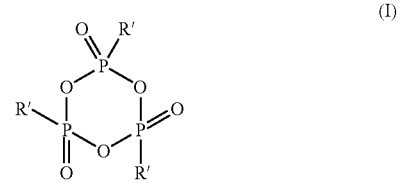

where R' is independently allyl, aryl or open-chain or branched $C_1$ to $C_{12}$-alkyl radicals, in particular $C_1$-$C_8$-alkyl radicals.

Particular preference is given to phosphonic anhydrides of the formula (I) in which R' is a methyl, ethyl, n-propyl, isopropyl, n-butyl, 2-butyl, isobutyl, pentyl, hexyl, especially an ethyl, propyl and/or butyl radical.

The elimination to nitriles (II) can generally be performed at temperatures in the range from −100 to +120° C.; preference is given to temperatures in the range from −30 to +30° C., lower temperatures generally being correlated with higher selectivities. The reaction time is dependent upon the temperature employed and is generally from 1 to 12 hours, in particular from 3 to 6 hours.

The addition of amines is generally not required, but may prove to be advantageous in the individual case. The amines used are generally amines of the formula (III)

where $R^2$ is H, allyl, aryl or open-chain, cyclic or branched $C_1$ to $C_{12}$-alkyl radicals, aryloxy, allyloxy or alkoxy having open-chain, cyclic or branched $C_1$- to $C_{12}$-alkyl radicals, or a combination of the substituents mentioned.

Particular preference is given to amines of the formula (III) in which $R^2$ is an H, methyl, ethyl, n-propyl, isopropyl, n-butyl, 2-butyl, isobutyl, pentyl, hexyl, phenyl, in particular an H, ethyl, n-propyl, isopropyl, n-butyl, 2-butyl, isobutyl or phenyl, or a combination of the substituents mentioned.

The cyclic phosphonic anhydride can be added to the reaction medium either as a melt or as a liquid mixture dissolved in a solvent.

Suitable solvents are those which do not give rise to any side reactions with the phosphonic anhydride; these are all aprotic organic solvents, for example ligroin, butane, pentane, hexane, heptane, octane, cyclobutane, cyclopentane, cyclohexane, cycloheptane, cyclooctane, dichloromethane, chloroform, carbon tetrachloride, 1,2-dichloroethane, 1,1,2,2-tetrachloroethane, methyl acetate, ethyl acetate, propyl acetate, butyl acetate, dimethylformamide, diethylformamide, dimethylacetamide, diethylacetamide, diethyl ether, diisopropyl ether, tert-butyl methyl ether, THF, dioxane, acetonitrile or mixtures thereof; particular preference is given to dichloromethane, chloroform, ethyl acetate, propyl acetate, butyl acetate, dimethylformamide, diethyl-formamide, dimethylacetamide, diethylacetamide, diiso-propyl ether, tert-butyl methyl ether, THF, dioxane, acetonitrile or mixtures thereof; very particular preference is given to dichloromethane, chloroform, ethyl acetate, butyl acetate, dimethylacetamide, tert-butyl methyl ether, THF, dioxane, acetonitrile or mixtures thereof; especially preferred are THF, ethyl acetate or butyl acetate.

The phosphonic anhydride is added generally in at least one third of the stoichiometric amount in relation to the starting compound, but may also be added in a superstoichiometric amount, for example in a ratio of 1 starting compound:1.2 T3P® (cyclic propanephosphonic anhydride).

The reactions are preferably carried out in such a way that the corresponding starting compound is added in a suitable solvent to T3P® at the reaction temperature.

The reaction product is preferably isolated by hydrolysis and simple phase separation, since the conversion products of the phosphonic anhydrides are generally very water-soluble. Depending on the nature of the product to be isolated, post-extractions may also be required. The phosphonic anhydride conversion product formed often does not disrupt subsequent reactions, so that even the direct use of the resulting reaction solutions often brings very good results.

All procedures mentioned are notable for very good yields (typically 90-100%, in particular >95%) in the simultaneous absence of side reactions and epimerizations. The selectivities of the inventive reaction are in the range of 97-100%, in particular 99-100%.

The process according to the invention will be illustrated in detail by the examples which follow without restricting the invention thereto:

EXAMPLE 1

Elimination of Benzaldehyde Oxime to Benzonitrile 1 mol of T3P® in ethyl acetate (50% w/w) is cooled to 0° C. Benzaldehyde oxime is added dropwise to this solution and the mixture is stirred at this temperature for 3 hours. At this time, the reaction GC showed a conversion of 100%. After warming to room temperature, 180 ml of water were added and the phases were separated. After the solvent had been condensed off, the benzonitrile remained in a yield of 97%, GC purity 99% (a/a).

EXAMPLE 2

Elimination of Fufural Oxime to 2-cyanofuran 1 mol of T3P® in ethyl acetate (50% w/w) is cooled to 0° C. Fufural oxime is added dropwise to this solution and the mixture is stirred at this temperature for 3 hours. At this time, the reaction GC showed a conversion of 100%. After warming to room temperature, 180 ml of water were added and the phases were separated. After the solvent had been condensed off, the 2-cyanofuran remained in a yield of 97%, GC purity 99% (a/a).

EXAMPLE 3

Elimination of Octanol Oxime to Octanenitrile 1 mol of T3P® in ethyl acetate (50% w/w) is cooled to 0° C. Octanol oxime is added dropwise to this solution and the mixture is stirred at this temperature for 3 hours. At this time, the reaction GC showed a conversion of 100%. After warming to room temperature, 180 ml of water were added and the phases were separated. After the solvent had been condensed off, the octanenitrile remained in a yield of 97%, GC purity 99% (a/a).

The invention claimed is:

1. Process for preparing nitriles of the formula (II)

said process comprising reacting aldehyde oximes (R1CH=N—OH)

with cyclic alkylphosphonic anhydrides at a reaction temperature in the range from −100 to +120° C., where $R^1$ is H, a linear or branched $C_1$-$C_{12}$-alkyl radical, a $C_3$-$C_{10}$-cycloalkyl radical, alkenyl radical or an aryl or heteroaryl radical.

2. The process as claimed in claim 1, wherein the cyclic alkylphosphonic anhydride is a 2,4,6-substituted 1,3,5,2,4,6-trioxatriphosphinane 2,4,6-trioxide of the formula (I)

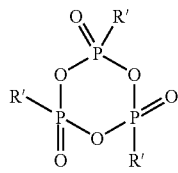

(I)

where R' is independently allyl, aryl or open-chain or branched $C_1$ to $C_{12}$-alkyl radicals.

3. The process as claimed in claim 2, wherein R' is selected from one or more of a methyl, ethyl, n-propyl, isopropyl, n-butyl, 2-butyl, isobutyl, pentyl, or hexyl, radical.

4. The process as claimed in claim 1, wherein the reaction is performed in the presence of an amine base of the formula (III)

$NR^2{}_3$ (III)

where $R^2$ is H, allyl, or open-chain, cyclic or branched $C_1$ to $C_{12}$-alkyl radicals, aryloxy, allyloxy or alkoxy having open-chain cyclic or branched $C_1$ to $C_{12}$-alkyl radicals, or a combination thereof.

5. The process as claimed in claim 1, wherein the cyclic alkylphosphonic anhydride is added to the reaction solution either as a melt or dissolved in a solvent.

6. The process as claimed in claim 5, wherein the cyclic alkylphosphonic anhydride is added in a solvent and the solvent is aprotic.

7. The process as claimed in claim 1, wherein the aldehyde oxime is heated to the reaction temperature before the cyclic alkylphosphonic anhydride is added.

8. The process as claimed in claim 1, wherein the cyclic alkylphosphonic anhydride is used in one third of the stoichiometric amount up to a superstoichiometric amount in relation to the aldehyde oxime.

9. The process as claimed in claim 2, wherein $R^1$ is selected from one or more of an ethyl propyl, or butyl radical.

* * * * *